United States Patent [19]

Speaker et al.

[11] Patent Number: 4,797,234

[45] Date of Patent: Jan. 10, 1989

[54] PRODUCTION OF SUSTAINED RELEASE COMPOSITION FROM SALT-FORM REACTANTS

[75] Inventors: Tully J. Speaker; Tychó J. Speaker, both of Philadelphia, Pa.; John H. Collett, Sale, England

[73] Assignee: Temple University, Philadelphia, Pa.

[21] Appl. No.: 64,859

[22] Filed: Jun. 19, 1987

[51] Int. Cl.$^4$ .......................... A61K 9/50; A61K 9/62; A61K 9/66; B01J 13/02

[52] U.S. Cl. ..................................... 264/4.1; 424/461; 424/493; 427/213.31; 428/402.21; 428/402.24; 514/963

[58] Field of Search ................ 427/213.3; 428/402.21, 428/402.24; 424/461, 493; 514/963

[56] References Cited

U.S. PATENT DOCUMENTS

| | | | |
|---|---|---|---|
| 3,575,882 | 4/1971 | Vandegaer et al. | 428/402.24 X |
| 3,909,441 | 9/1975 | Ohyama et al. | 428/402.24 X |
| 3,959,457 | 5/1976 | Speaker et al. | 428/402.24 X |
| 4,003,846 | 1/1977 | Kuhn et al. | 428/402.24 X |
| 4,324,683 | 4/1982 | Lim et al. | 428/402.24 X |

FOREIGN PATENT DOCUMENTS 0128324  7/1984  Japan .................................. 424/493

OTHER PUBLICATIONS

Mar.: *Advanced Organic Chemistry*, Third Edition, John Wiley & Sons, New York (1985) pp. 795, 800–802.
*Mitsubishi Acetate*, Translation of J5-9128-324.

*Primary Examiner*—Richard D. Lovering
*Attorney, Agent, or Firm*—Ratner & Prestia

[57] ABSTRACT

Sustained-released delivery forms comprising the reaction product of a Lewis acid salt with a Lewis base salt at the phase interface of their respective aqueous and non-aqueous solution to form an anisotropic high molecular weight salt of the acid and base and a neutral salt of the inorganic cation and anion in what is termed a "double decomposition" or "salt exchange" reaction.

7 Claims, No Drawings

PRODUCTION OF SUSTAINED RELEASE COMPOSITION FROM SALT-FORM REACTANTS

BACKGROUND OF THE INVENTION

This invention pertains to novel microparticulate material, the particles of which are sometimes referred to as microcapsules and to a method for making such material. More specifically, this invention pertains to microcapsular material comprising the reaction product of a salt form of a Lewis acid in an aqueous solution and the salt form of a Lewis base in a non-aqueous solution, wherein said microparticles may act as a carrier for diffusable reactants, such as chemicals and pharmaceuticals in order to serve as sustained or controlled release "microencapsulated" delivery forms.

Microencapsulation is a technique of enclosing core materials within a polymeric membrane to produce microparticles. The encapsulated material may be released over a period of time by diffusion or immediately by crushing or by digesting the shell-like wall of the microparticle. These types of microparticles are used extensively in the dye, and the food and cosmetic industries.

In the pharmaceutical industry, considerable interest has been generated by the use of microparticles as sustained release drug delivery formulations. However, many microparticle formulations are of limited utility because of their relatively large particle size. A particle size of greater than that of an erythrocyte (about 7 microns) is not suitable to be injected intraveneously.

Further problems with known prior art microparticulate material arise from the fact that generally such material tends to agglomerate, thus deleteriously affecting certain important properties of the materials such as dispersability. Additionally, microparticulate material which is of suitable size for injection may also be captured by the reticulo-endothelial system, which can have deleterious effects on blood clearance of the microparticle shell material and tissue distribution of the encapsulated core material.

A specific type of microparticulate material and a method of making such a material is disclosed in U.S. Pat. No. 3,959,457 (of common inventorship and assignment herewith). This material is comprised of the reaction product produced at the inter-phase boundary of a finely dispersed emulsion, comprising:

(I) a water immiscible solution of an organic polyfunctional Lewis base in a low boiling point, slightly polar, organic solvent; and (II) an aqueous solution of a partially hydrophilic, partially lipophilic, polyfunctional Lewis acid.

Microparticles of this type comprise a multiplicity of closed structures formed of lattice-like high molecular weight salt molecules of the Lewis acid and Lewis base, through which an encapsulated core material diffuses. The rate of diffusion is controlled by both the particle or molecular size of the encapsulated compound and by the openness of the lattice or network of molecules comprising the particle walls. The degree of openness of the lattice is controlled by the spacing of reactive sites on the high molecular weight polyfunctional Lewis acids and by the thickness of the particle walls.

BRIEF DESCRIPTION OF THE INVENTION

This invention comprises Lewis acid—Lewis base salt microparticulate materials of the type referred above wherein both the Lewis acid and the Lewis base reactants are utilized in their salt forms. The salt forms of the Lewis acid and Lewis base react to form a new anisotropic salt of the acid and base and a neutral salt of the inorganic cation and anion in what is sometimes termed a "double decomposition" or "salt exchange" reaction.

DETAILED DESCRIPTION OF THE INVENTION

Generally, microparticles of the type to which this invention is directed are made as follows:

An non-aqueous solution of a salt form of a Lewis base, such as benzalkonium chloride, is added to an aqueous solution of a salt form of a Lewis acid, such as sodium carboxymethylcellulose. The solutions are combined with rapid stirring to produce a finely dispersed emulsion of organic phase droplets in a continuous aqueous phase. Included in the non-aqueous solvent is a core material such as a drug. For purposes of sustained release of the core material, it must be of such molecular size that it will be able to diffuse out of the individual microparticulate material.

In the organic phase droplets of the finely dispersed emulsion of the aqueous and non-aqueous solutions, the polyfunctional Lewis base is drawn to the surface of the droplet by the polar attraction of the surrounding aqueous phase. In the aqueous phase, the partially hydrophilic, partially lipophilic, polyfunctional Lewis acid is drawn, due to its partially lipophilic characteristic towards the interface between the organic droplet and the surrounding aqueous phase where it reacts, presumably through dipole and/or ionic bonding, with the polyfunctional Lewis base concentrated on the outer surfaces of the organic phase droplets adjacent the interface, to produce a shell-like insoluble particle generally corresponding in shape and size to the organic droplets. Each of these shell-like particles is thought to consist of an open network, or lattice, of molecules of a dipole and/or ionic salt.

The reaction of the polyfunctional Lewis acid moieties and polyfunctional Lewis base moieties is thought to be essentially a two step reaction sequence resulting in the formation of anisotropic salt films in small spherical or sphere like shapes sometimes referred to as microcapsules, and neutral inorganic salts in aqueous solution. The generalized reaction sequence is more clearly set out in U.S. Pat. No. 3,959,457 except that salt-form reactants were not suggested therein and indeed had not been successfully utilized prior to the present invention.

This invention describes the use of two pairs of oppositely charged species (namely, the salt form of a Lewis acid moiety and the salt form of a Lewis base moiety), which interact to generate two new pairs of oppositely charged ions. One new pair of oppositely charged ions (e.g., the benzalkonium salt of carboxymethylcellulose or benzalkonium methylcellulose carboxylate) is poorly soluble at the phase interface and precipitates to form the wall of the microcapsule. The other new pair of oppositely charged ions (e.g., sodium chloride) is typically fairly water soluble and readily dissolves in the aqueous medium. Thus, the salt ion of the Lewis acid reacts with the salt ion of the Lewis base to form a new ansiotropic salt of the acid and base and a neutral salt of the inorganic cation and anion in a "double composition" reaction.

It should be noted that U.S. Pat. No. 3,959,457 teaches, inter alia, the use of certain quaternary ammonium chlorides (e.g., methylrosaniline chloride) as Lewis base wall forming reagents in reactions with Lewis acid reagents such as arabic acid to form microcapsules much like those described herein. The reaction there described involves the transfer of a proton from a free carboxyl group of the acid (e.g., arabic acid) to a proton accepting function (a nitrogenous substituent of the methylrosaniline chloride) to form at the phase interface a pair of oppositely charged ionic species. The quaternary ammonium group is the positively charged salt constituent of methylrosaniline chloride but, as such, is non-reactive in the above reaction sequence. Thus, this compound does not function as a Lewis base salt in accordance with the present invention.

More explicitly, the quaternary ammonium group is already positively charged and therefore cannot accept a proton from some acidic function to generate a new pair of oppositely charged species. However, the basic functions of methylrosaniline chloride and other substituted rosaniline compounds can and do. In so doing only the basic functions of these compounds participate in the wall forming reaction.

Analogously, but developing the argument with the complementary set of ionic species, piperazine molecules readily accept protons from molecules of carboxymethylcellulose to generate new pairs of oppositely charged ions and thus, participate in the wall forming reaction. However, sodium carboxymethylcellulose lacks protons to donate to piperazine and thus cannot serve in the wall forming reaction.

General Procedure for Forming Microcapsules

The following are descriptions of examples of the process of the present invention for making microparticulate material. In all instances where an aqueous solution is utilized as the continuous phase for the dispersion or emulsification of a second solution of materials dissolved in an organic solvent, it is preferred, but not essential, that the organic solvent be slowly and steadily added to the aqueous solution over a period of approximately 30 seconds. In all instances, solutions are prepared and reactions take place at room temperature, unless otherwise stated. Any of several means to disperse or emulsify the organic solution in the aqueous medium may be employed including:

a. vigorously stirring the solution with a magnetically driven stirring bar at a nominal shear rate, generally 700 or more cm/s;

b. vigorously mixing the solution with a multi-orifice axial turbine (such as a Brinkmann homogenizer PT10/30 and generator PST/10, Brinkmann Instruments, Westbury, N.Y.) at a nominal setting of 5; or c. vigorously agitating the solutions with an ultrasonic probe (such as Heat Systems model W185D, Ultrasonics, Inc., Plainview, N.Y.) at a nominal output of 100 watts.

An aqueous solution of sodium carboxymethylcellulose was prepared by adding to 0.01 gram of sodium carboxymethyl cellulose, enough water to make 10 mL. A non-aqueous solution was also prepared by adding (in an amount stoichiometrically equivalent to the sodium carboxymethyl cellulose), anhydrous benzalkonium chloride and 1.0 g of a core material (acetanilide) in enough dichloromethane to make 10 ml of solution.

The aqueous and non-aqueous solutions were then combined in a container and continuously agitated for approximately one minute, to produce an emulsion of organic droplets, approximately 5 microns in diameter, dispersed in and surrounded by continuous phase aqueous solution.

Upon standing after agitation the newly formed microcapsules were allowed to separate from the bulk of the aqueous phase and settle to the bottom of the container. The separation was speeded by centrifugation. The clear supernatant aqueous phase was then removed along with any residual clear non-aqueous organic phase which may have separated. Unreacted or excess reaction components were then removed by dispersing the microcapsules in an equal amount of water and again removing the supernatant liquid from the packed microcapsules. Residual dichloromethane was removed by evaporation upon exposure of the microcapsules to the atmosphere. The product comprised a flowable concentrate of microparticulate material consisting of microcapsules of shell-like films surrounding the (acetanilide) core material.

Other salt form microcapsules with differing wall components may be made by substituting the Lewis base and Lewis acids salt forms with such compounds as, cetylpyridinium chloride for benalkonium chloride, or the sodium salt of a poly-acrylic acid or the sodium salt of polyoxyethylene cross-linked with polyacrylic acid (e.g. Carbopol 934, a product of B. F. Goodrich) for sodium carboxymethylcellulose. Futhermore, microcapsules may also be formed by substituting both the benzalkonium chloride and sodium carboxymethylcellulose with cetylpyridinium chloride and the sodium salt of a poly-acrylic acid or the sodium salt of polyoxyethylene cross-linked with poly-acrylic acid, respectively.

Microcapsules made from reactants in their salt forms as taught by the instant invention may be readily made in the range of sizes from below 1 micron to above 1000 microns by modifying dispersion techniques (i.e. intensity and/or duration) to produce emulsion droplets of the appropriate size. These new microcapsules have very high internal to wall volume ratios, thus high core loading fractions may be attained. Electron micrographs show the walls can be made only a fraction of a micron thick with the central volume clearly demarked from the wall proper. Furthermore, use of the new wall components can confer advantageous properties on the resultant microcapsules which are not present in the microparticles described in U.S. Pat. No. 3,959,457. For example, the microcapsules made by reaction of benzalkonium chloride and sodium carboxymethylcellulose, as described above, are markedly more stable then are those derived from piperazine and arabic acid, the preferred materials in U.S. Pat. No. 3,959,457. Microcapsules with walls of benzalkonium methylcellulose carboxylate are stable at 50 C. (122 F.) for many hours, while microcapsules with walls of piperazine arabate degrade after a few minutes at that temperature.

Thus, the microcapsules of the instant invention, as exemplified by the preferred materials, have significantly different characteristics from those of U.S. Pat. No. 3,959,457.

While this invention has been described with reference to specific, and particularly, preferred embodiments thereof, it is not limited thereto and the appended claims are intended to be construed to encompass not only the specific forms and variants of the invention shown but to such other forms and variants as may be devised by those skilled in the art without departing from the true spirit and scope of the invention.

We claim:

1. A method for producing a microcapsule comprising an anisotropic salt film for the gradual release of an encapsulated core material, consisting essentially of reacting (a) a partially hydrophilic, partially lipophilic polyfunctional Lewis acid salt in aqueous medium; and (b) a core material and a Lewis base salt in a water-immiscible, slightly polar, organic solvent for the base; in the form of an emulsion consisting essentially of a continuous aqueous phase of Lewis acid salt and water, and a discontinuous droplet phase of core material, Lewis base salt, and organic solvent, to form an anisotropic Lewis acid/Lewis base salt film semipermeable to and encapsulating the core material, and a neutral salt.

2. The method of claim 1 wherein the organic solvent is selected from the group consisting of bromoform, chloroform, dichloromethane, dichloroethane, diethyl ether, diisopropyl ether, methylethylketone and nitrobenzene.

3. The method of claim 2, wherein the organic solvent is dichloromethane.

4. The method of claim 1, wherein the Lewis base salt is benzalkonium chloride or cetylpyridinium chloride.

5. The method of claim 4, wherein the Lewis acid salt is sodium carboxymethylcellulose.

6. The method of claim 1, wherein the Lewis acid salt is sodium carboxymethylcellulose, a sodium salt of polyacrylic acid, or a sodium salt of a polyoxyethylene cross-linked polyacrylic acid.

7. The method of claim 1, wherein the core material is a pharmaceutical.

* * * * *